US006105713A

United States Patent [19]

Brimhall et al.

[11] Patent Number: 6,105,713

[45] Date of Patent: Aug. 22, 2000

[54] COVER MOVABLE BY ROTATION FORMING A CERUMEN BARRIER IN A HEARING AID

[75] Inventors: Owen D. Brimhall, South Jordan; Gregory N. Koskowich; Robert P. Wyckoff, both of Salt Lake City; James M. Nee, West Jordan, all of Utah

[73] Assignee: Sonic Innovations, Inc., Salt Lake City, Utah

[21] Appl. No.: 09/156,212

[22] Filed: Sep. 17, 1998

[51] Int. Cl.[7] .......... A61B 7/02

[52] U.S. Cl. .......... 181/135; 381/325

[58] Field of Search .......... 181/129, 135; 381/322, 325, 328

[56] References Cited

U.S. PATENT DOCUMENTS

| | | |
|---|---|---|
| D. 355,702 | 2/1995 | Johnson . |
| 3,197,577 | 7/1965 | Kuklock . |
| 3,415,246 | 12/1968 | Hill . |
| 3,457,375 | 7/1969 | Haggerty . |
| 3,598,928 | 8/1971 | Hickox . |
| 3,872,559 | 3/1975 | Leight . |
| 3,881,570 | 5/1975 | Lewis . |
| 3,976,848 | 8/1976 | Estes . |
| 4,160,449 | 7/1979 | Wade . |
| 4,193,396 | 3/1980 | Wacker . |
| 4,253,452 | 3/1981 | Powers et al. . |
| 4,293,355 | 10/1981 | Wacker . |
| 4,434,794 | 3/1984 | Leight . |
| 4,440,982 | 4/1984 | Kaanders et al. . |
| 4,553,627 | 11/1985 | Gastmeier et al. . |
| 4,582,053 | 4/1986 | Wilson . |
| 4,774,938 | 10/1988 | Leight . |
| 4,800,982 | 1/1989 | Carlson . |
| 4,870,689 | 9/1989 | Weiss . |
| 4,879,750 | 11/1989 | Nassler . |
| 4,937,876 | 6/1990 | Biermans . |
| 4,945,569 | 7/1990 | Kulman . |
| 4,953,215 | 8/1990 | Weiss et al. . |
| 4,972,488 | 11/1990 | Weiss et al. . |
| 4,987,597 | 1/1991 | Haertl .......... 381/325 |
| 5,074,375 | 12/1991 | Grozil . |
| 5,099,947 | 3/1992 | Guggenberger et al. . |
| 5,105,904 | 4/1992 | Olsen . |
| 5,113,967 | 5/1992 | Killion et al. . |
| 5,131,128 | 7/1992 | Bisgaard et al. . |
| 5,133,016 | 7/1992 | Clark . |
| 5,166,659 | 11/1992 | Navarro . |
| 5,188,123 | 2/1993 | Gardner, Jr. . |
| 5,203,352 | 4/1993 | Gardner, Jr. . |
| 5,278,360 | 1/1994 | Carbe et al. . |
| 5,293,008 | 3/1994 | Danielsen . |
| 5,319,163 | 6/1994 | Scott . |
| 5,327,500 | 7/1994 | Campbell . |
| 5,401,920 | 3/1995 | Oliveira . |
| 5,452,731 | 9/1995 | Dickman . |
| 5,488,961 | 2/1996 | Adams . |
| 5,530,763 | 6/1996 | Aebi et al. . |
| 5,535,282 | 7/1996 | Luca . |
| 5,864,628 | 1/1999 | Posen .......... 381/325 |

*Primary Examiner*—Khanh Dang
*Attorney, Agent, or Firm*—D'Alessandro & Ritchie

[57] ABSTRACT

A movable cover that pivots over a receiver port in the hearing aid shell forms a cerumen barrier. Alternatively, the cerumen barrier includes both a movable cover that pivots over a receiver port in the hearing aid shell and a deformable grommet and membrane assembly that is disposed over the receiver port.

17 Claims, 1 Drawing Sheet

COVER MOVABLE BY ROTATION FORMING A CERUMEN BARRIER IN A HEARING AID

BACKGROUND OF THE INVENTION

1. Field of the Invention

The present invention relates to a cerumen barrier for a hearing aid. More particularly, the present invention relates to a cover movable by rotation over the receiver port in the shell of a hearing aid forming a cerumen barrier.

2. The Prior Art

With the vast improvement in integrated circuit technologies and signal processing capabilities in recent years, the focus of hearing aid technologies has shifted from a behind-the-ear hearing aid resting on the visible external ear to an in-the-ear hearing aid that is inserted almost entirely into the ear canal. In a typical in-the-ear hearing aid, a microphone disposed within the hearing aid shell and adjacent to an input sound port receives an acoustic signal and transduces the acoustic signal into an electrical signal. The electrical signal is processed, and the processed signal is output to an electro-acoustic output transducer that converts the processed electrical signal to an acoustic signal. A sound passage tube connected to the output transducer passes the acoustic signal through a sound outlet port in the tip of the hearing aid shell. The sound outlet port is usually proximal to the ear drum of the hearing aid user, and is positioned approximately mid-canal.

An ear canal into which an in-the-ear hearing aid is disposed has a bent shape and consists essentially of two portions. The first portion is closest to the external ear and extends typically a little over a centimeter into the ear canal, has soft tissue between the skin and the underlying bone to form a padded area, and has tiny hairlike projections. Cerumen or wax is produced in this portion of the ear canal. The second portion is closest to the ear drum and comprises skin over bone, with little soft tissue to offer padding between the skin and bone. Because of the lack of padding in the second portion, the skin in the second portion is quite sensitive to any foreign body that is placed against it. As such, in-the-ear hearing aids are typically placed such that the portion of the hearing aid pressing against the hearing canal does not extend further than the first portion of the ear canal.

Unfortunately, the cerumen which is produced in the first portion of the ear canal can then more readily cause problems with the operation of the hearing aid. There are at least two problems well known to those of ordinary skill in the art that cerumen can cause. First, is a clogging of the outlet sound port which reduces sound transmission from the hearing aid to the hearing aid user. Second is cerumen travelling down the sound tube to impair, disable or ruin the electro-acoustic transducer. As a result, a wide variety of apparatus have been proposed in the prior art that act as a barrier between the cerumen and the sound tube.

In the examples of the various cerumen barriers given below, the ease of cleaning and replacement, frequency of cleaning and replacement, and acoustic attenuation are just a few of the design issues that were contemplated. The various cerumen barriers include complex mechanical arrangements that form a difficult or tortuous path for cerumen to travel along to get to the sound outlet port, a filter, a torturous path in combination with a filter, grooves or areas in the barrier designed to collect cerumen, etc.

As examples of a tortuous path cerumen barrier, U.S. Pat. No. 4,870,689 describes a housing that is positioned within the tip of the hearing aid and has a plurality of projections within the substantially cylindrical housing to impede and accumulate cerumen entering the housing, and U.S. Pat. No. 5,105,904 describes the combination of a component and a cap, wherein the component is insertable into the tip of a hearing aid and has a number of circumferentially spaced angle brackets and radially projecting bracket locking detents and a cap that fits over the angle brackets and onto the locking detents.

As an example of a filter, U.S. Pat. No. 5,401,920 describes a cerumen barrier which comprises a thin flexible membrane one surface of which has a pressure sensitive adhesive layer so that the membrane may be affixed to the tip of the hearing aid. And as examples of a tortuous path combined with a filter U.S. Pat. No. 4,553,627 describes a cerumen barrier having a stem portion and a head portion, wherein the stem portion is inserted into the tip of the hearing aid and has an axial tube with an acoustic filter disposed therein and which communicates with a cross passage which extends through the head portion, and U.S. Pat. No. 4,972,488 describes a housing that is positioned within the tip of the hearing aid and has a plurality of projections within the substantially cylindrical housing to impede and accumulate cerumen entering the housing, and a screen to further impede and accumulate cerumen.

As examples of cerumen barriers that have specific places designed to accumulate cerumen, U.S. Pat. No. 4,953,215 describes a non-porous membrane which covers an electro-acoustics transducer which projects into a sound conducting channel, wherein the non-porous membrane has a bore that communicates with the channel, and U.S. Pat. No. 4,879,750 discloses a perforated cap which is secured to a protrusion on the tip of the hearing aid and has a substantially flat end plate adjacent to the protrusion which bears a groove for collecting cerumen.

As further examples of cerumen barriers, U.S. Pat. No. 4,945,569 describes a tube section which projects beyond the tip of the hearing aid and further has a yoke formed over the tube of the tube extending from the tip of the hearing aid. U.S. Pat. No. 5,099,947 describes a cerumen guard which is formed as a coil of wire cone that is interference fitted into the receiver of a hearing aid. U.S. Pat. No. 5,278,360 describes a cerumen trap which has a body that is inserted into and affixed to the tip of a hearing aid shell and which communicates with the sound tube and a bridge that is formed integrally with the body and extending over the opening in the body, wherein the bridge includes both a bar and a shielding member. U.S. Pat. No. 5,293,008 discloses a cerumen trap which includes a piston or plug shaped member for pushing cerumen out of the cerumen trap. And U.S. Pat. No. 5,327,500 describes a sound outlet base and a barrier door, wherein the sound outlet base is inserted and secured into the sound outlet port of the hearing aid shell and the barrier door is inserted into the counterbore of the sound outlet base.

Though each of these cerumen barrier designs to some degree address one or all of the design issues set forth above and other design issues as well, their exists the need for a cerumen barrier that prevents cerumen and moisture from entering the sound outlet passage, may be easily replaced, and provides a desired acoustic response.

BRIEF DESCRIPTION OF THE INVENTION

According to the present invention, in a first embodiment, a movable cover that pivots over a receiver port in the hearing aid shell forms a cerumen barrier. In an second embodiment, the cerumen barrier includes both a movable cover that pivots over a receiver port in the hearing aid shell and a deformable grommet and membrane assembly that is disposed over the receiver port.

DETAILED DESCRIPTION OF A PREFERRED EMBODIMENT

Those of ordinary skill in the art will realize that the following description of the present invention is illustrative only and not in any way limiting. Other embodiments of the invention will readily suggest themselves to such skilled persons.

Figure 1:
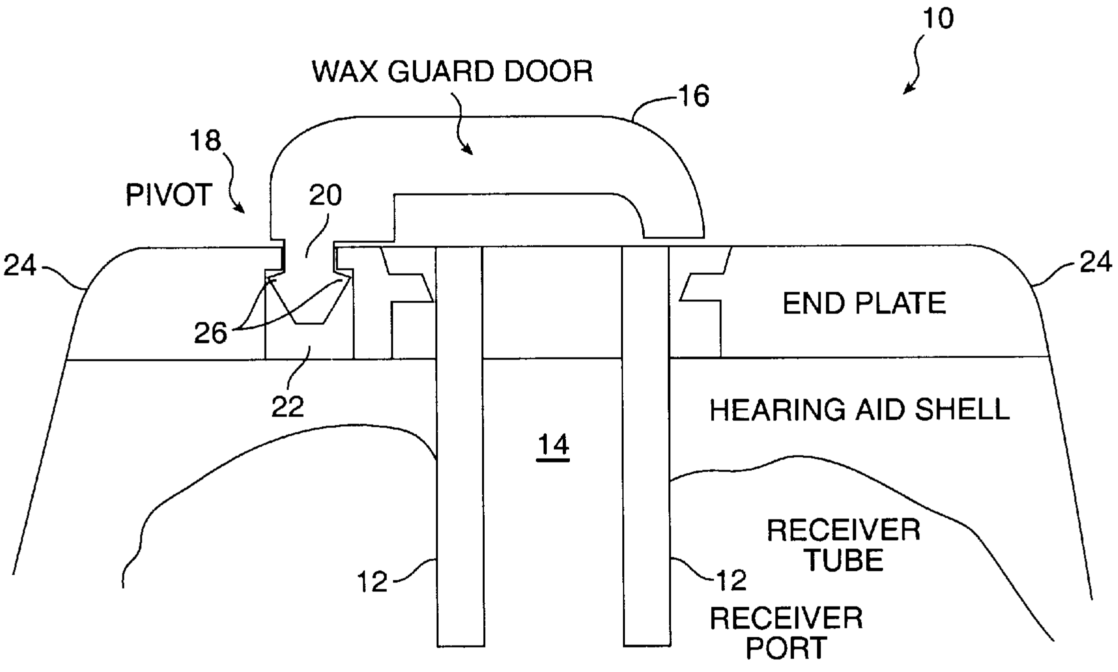
FIG. 1 illustrates in cross-section a cerumen barrier according to a first embodiment of the present invention.

In FIG. 1, a cross section of the end of a hearing aid shell 10 is depicted in cross section. Formed at the end of the hearing aid shell 10 by a receiver tube 12 disposed in the hearing aid shell 10 is a receiver or sound outlet port 14 that communicates the acoustic signal generated by the hearing aid to the ear drum of the hearing aid user. According to the present invention, a movable cover 16 is positioned over the receiver port 14 to act as cerumen barrier in preventing cerumen and debris from entering the receiver port 14. The movable cover 16 preferably has cup shape so that a small space is formed between the lower surface of the movable door 16 and the top of the opening of the receiver port 14. The movable cover 16 protects the receiver port 14 from the direct scooping of cerumen into the receiver port 14 during insertion of the hearing aid into the ear.

The movable cover 16 can be rotated over the tip of the hearing aid shell 10 about a pivot 18 that is formed by an arm 20 of the movable cover 16 disposed in the recess of 22 of an endplate 24 formed on the end of the hearing aid shell 10. The axis of the arm 20 is substantially orthogonal to the plane of the upper surface of the movable cover 16. With the arm 20 positioned in the recess 22, the movent of the movable cover 16 is effectively prevented from any movement except for rotation around the pivot 18. Some small amount of movement in an up and down or lateral movement may be achieved, but the primary movement of moveable cover 16 is in rotation about the pivot 18. By rotating the movable cover 16 along the surface of the hearing aid shell and away from above the receiver port 14, any cerumen or debris that has accumulated in the receiver port 14 may be readily removed.

According to the preferred embodiment, the endplate 24 is fastened to the end of hearing aid shell by adhesive bonding. The endplate 24 is then trimmed to match the profile of the ear canal. Once the endplate 24 is bonded to the tip of the hearing aid shell 10 and trimmed to match the ear canal, the arm 20 of movable cover 16 can be snapped into place so that flanges 26 on the arm 20 to form the pivot 20 and to prevent the movable cover 16 from being displaced from the recess 22 in the end plate 24. In the first embodiment of the present invention, the sound tube 12 extends past the tip of the hearing aid shell 10 to be flush with the outside edge of the endplate 24.

Figure 2:
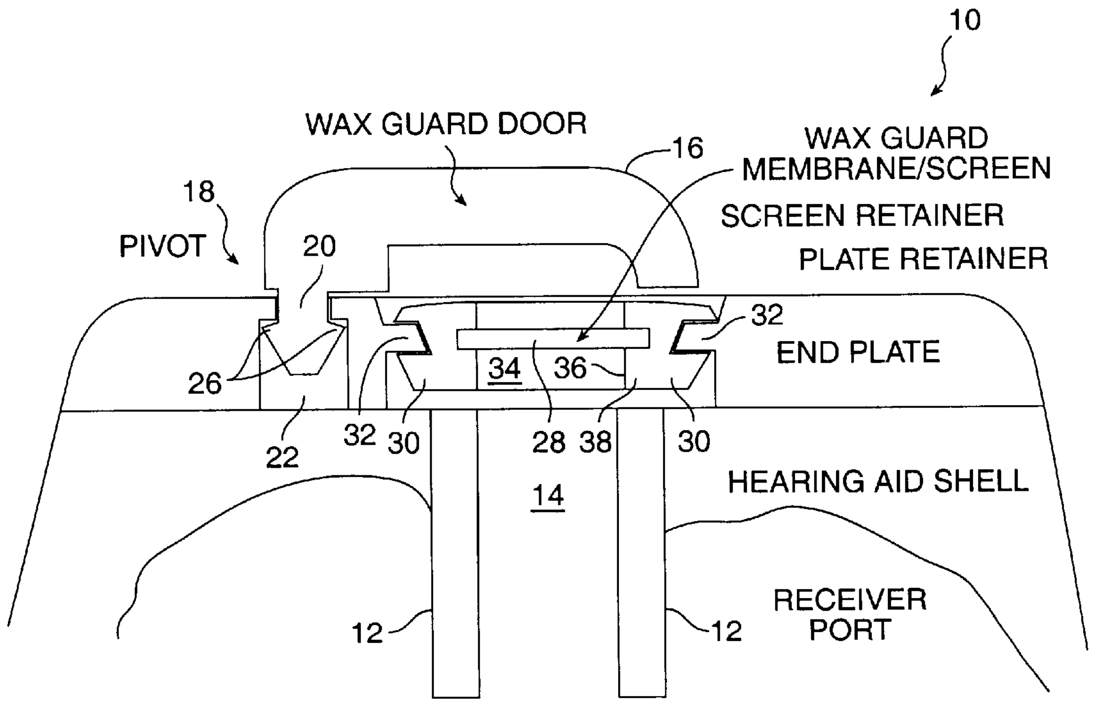
FIG. 2 illustrates in cross-section a cerumen barrier according to a second embodiment of the present invention.

As is well understood by multitudes of hearing aid users, and those of ordinary skill in the art, the process of keeping the sound tube of a hearing aid free from cerumen and other debris is a nearly continuous exercise. According to a second embodiment of the present invention depicted in FIG. 2, in addition to the movable cover 16 illustrated in FIG. 1, a membrane 28 formed in a deformable grommet 30 may be readily fitted over a retaining member 32 formed in the endplate 24. When the wax build-up on the membrane 28 becomes too great, the integrated membrane 28 and grommet 30 assembly may be removed from the retaining member 32, be disposed of and replaced. The integrated membrane 28 and grommet 30 assembly form a sound passage 34 that is disposed above a sound passage tube 12 in the hearing aid shell 10. According to the present invention, the membrane 28 provides a barrier to both cerumen and to liquids.

The deformable grommet 30 in the preferred embodiment is formed from silicone. It will be appreciated, however, by those of ordinary skill in the art that the deformable grommet 30 could be formed from other elastomeric materials. The shape of the deformable grommet 30 is somewhat cylindrical. The passage 34 formed by the inner portion of wall 36 of the deformable grommet 30 is essentially uniform in diameter, and in the preferred embodiment, has an opening of about 0.051 inches in diameter. The outer portion of the grommet 30 has a tapered undercut leading to a ring shaped cutout in the middle section. The ring shaped cutout is shaped to mate with the shape of retaining member 32 to form a locking detent.

According to the present invention, the deformable grommet 30 and membrane 28 assembly may be fitted into the tip of the hearing aid shell 10 by simply pressing the deformable grommet 30 past the retaining member 32. As the deformable grommet 30 is pushed past the retaining member 32, the wall 36 deforms and is forced inward. Once a lip 38 formed by the bottom of the ring shaped cutout in the outer portion of the wall 36 slides past the lower edge of the retaining ring 14, the wall 30 moves radially outward to return to its original shape. The outer portion of the wall 30 which has been shaped to follow the contour of the retaining member 32 presses against the retaining member 32 to apply and maintain a mechanical force. It will be appreciated by those of ordinary skill in the art that other apparatus suitable for fastening the deformable grommet and membrane 28 assembly in the tip of the hearing aid shell 10 may be employed.

According to the present invention, the membrane 28 is preferably a woven polyester or nylon screen, such as manufactured by Tetko with the trade names PeCap and Nitex. Membrane 28 has advantageous physical properties in it that permits good sound transmission, and further, has been coated to be both hydrophobic and oleophobic. Membrane 28 is also classified as a technical vent that provides pressure equalization. The operation of the vent to perform pressure equalization is critical in maintaining transducer diaphragm integrity. The known uses of the material from which membrane 28 is formed include that of microphones, pressure valves and speaker covers. The maximum acoustic attenuation for both composite and pure tones occurring due to the action of the membrane 28 is less than about 1.0 dB from 300 hz to 6000 hz. It should be appreciated, that other materials known to those of ordinary skill in the art may be used to provide the functional characteristics of the membrane 28.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A hearing aid for insertion into an ear, said hearing aid comprising:

a shell enclosing the hearing aid, said shell including a tip region having a sound port, said sound port penetrating said shell;

a sound tube connecting said sound port with an internal portion of the hearing aid;

a cover pivotally mounted to said tip region, said cover moveable to cover said sound port;

a deformable grommet having a central aperture; and a cerumen barrier in the shape of a flat membrane disposed within said central aperture, said grommet disposed within said tip region adjacent to and outward of said input sound port.

2. A hearing aid according to claim 1, wherein the said tip region includes an end plate shaped to conform to the hearing canal of the ear and wherein said grommet is disposed within said end plate.

3. A hearing aid according to claim 2, wherein said end plate is fastened to said shell by an adhesive.

4. A hearing aid according to claim 2, wherein said cover is embedded in a recess of said end plate.

5. A hearing aid according to claim 1 wherein said cover is cup-shaped.

6. A hearing aid according to claim 5, wherein said cover forms a space between its lower surface and the sound port.

7. A hearing aid according to claim 1, wherein the said deformable grommet is cylindrical in shape and said grommet is formed of Silicone.

8. A hearing aid according to claim 1, wherein said grommet and membrane assembly are removably mounted.

9. A hearing aid according to claim 2, wherein said grommet has a tapered undercut leading to a ring-shaped cutout.

10. A hearing aid according to claim 9 wherein said ring-shaped cutout is shaped to mate with the shape of a retaining member disposed in said end plate to form a locking detent.

11. An in-the-ear hearing aid, comprising:

an outer shell;

an end plate disposed on said shell;

an output sound port disposed in said end plate;

a sound tube connecting an interior portion of the hearing aid with said end plate;

a grommet having a central aperture;

a cerumen barrier in the shape of a flat membrane disposed within said central aperture, said grommet disposed within an output aperture through said end plate; and a pivotally mounted cover protecting said output aperture.

12. A hearing aid according to claim 11, wherein the said grommet has a tapered undercut leading to a ring-shaped cutout.

13. A hearing aid according to claim 12 wherein said ring-shaped cutout is shaped to mate with the shape of a retaining member disposed in said end plate to form a locking detent.

14. A hearing aid according to claim 11, wherein said grommet is cylindrical in shape and formed of silicone.

15. A method of preventing ear wax buildup in an in-the-ear hearing aid having an outer shell with a sound outlet port coupled via a sound tube to an interior region of the hearing aid, said method comprising:

providing a pivotally mounted cover removably mounted to the shell and adapted to cover the sound outlet port; and blocking the sound tube with a grommet having aperture, said aperture having a cerumen barrier in the shape of a flat membrane disposed therein.

16. A method according to claim 15, further comprising:

cleaning the hearing aid by pivoting the cover to expose the sound outlet port.

17. A method according to claim 16, further comprising:

removing and cleaning the grommet to clear the hearing aid of ear wax.

* * * * *

UNITED STATES PATENT AND TRADEMARK OFFICE
CERTIFICATE OF CORRECTION

PATENT NO. : 6,105,713
DATED : August 22, 2000
INVENTOR(S) : Brimhall et al.

It is certified that error appears in the above-identified patent and that said Letters Patent is hereby corrected as shown below:

Column 1,
Lines 51-52, replace “outlet sound” with -- sound outlet --.

Column 3,
Line 4, replace “receiver” with -- sound --.
Line 7, replace “receiver” with -- sound --.
Line 9, replace “receiver” with -- sound --.
Line 27, delete “in cross section”.
Line 27, replace “end” with -- tip --.
Line 37, replace “receiver” with -- sound --.
Line 38, replace “receiver” with -- sound --.
Line 39, replace “receiver” with -- sound --.
Line 47, replace “movent” with -- movement --.
Line 54, replace “receiver” with -- sound --.

Signed and Sealed this

Thirteenth Day of August, 2002

*Attest:*

JAMES E. ROGAN

*Attesting Officer*

*Director of the United States Patent and Trademark Office*